United States Patent [19]

Prevost

[11] Patent Number: 5,417,102
[45] Date of Patent: May 23, 1995

[54] ON-LINE METHOD FOR MEASURING DENSITY OF SOLIDS IN REACTION PROCESS

[75] Inventor: Thomas H. Prevost, Bergen, N.Y.

[73] Assignee: Eastman Kodak Company, Rochester, N.Y.

[21] Appl. No.: 174,496

[22] Filed: Dec. 28, 1993

[51] Int. Cl.$^6$ .............................. G01N 9/20; B03D 1/00
[52] U.S. Cl. ................... 73/61.71; 209/166; 73/28.01; 73/31.07
[58] Field of Search ............... 73/61.71, 32 R, 23.2, 73/30.01, 28.01, 53.01, 31.07

[56] References Cited

U.S. PATENT DOCUMENTS

| 2,819,608 | 1/1958 | McLaren et al. | 73/38 |
| 3,339,399 | 9/1967 | Hubbard et al. | 73/30.01 |
| 3,368,393 | 2/1968 | Wilson et al. | 73/53.01 |
| 4,226,714 | 10/1980 | Furness | 210/723 |
| 4,263,010 | 4/1981 | Randolph | 23/230 |
| 4,336,143 | 6/1982 | Abbott | 210/740 |
| 4,726,896 | 2/1988 | Grove et al. | 209/166 |
| 4,731,176 | 3/1988 | Macdonald | 209/166 |

FOREIGN PATENT DOCUMENTS

| 10900 | 7/1963 | Japan | 73/61.71 |
| 184191 | 9/1966 | U.S.S.R. | 73/32 R |
| 1272174 | 11/1986 | U.S.S.R. | 73/61.71 |

Primary Examiner—Hezron E. Williams
Assistant Examiner—J. David
Attorney, Agent, or Firm—John R. Everett

[57] ABSTRACT

Herein is disclosed a differential densitometer for continuously measuring total undissolved solids in a liquid. The densitometer comprises:
a) a first densitometer having liquid inlet and outlet;
b) a second densitometer having liquid inlet and outlet; and
c) a filter connecting the outlet of the first densitometer to the inlet of the second densitometer.

7 Claims, 2 Drawing Sheets

ON-LINE METHOD FOR MEASURING DENSITY OF SOLIDS IN REACTION PROCESS

FIELD OF THE INVENTION

This invention relates to controlling the concentration of solids in chemical manufacturing processes.

BACKGROUND

To obtain optimum control of many chemical processes, it is essential to monitor the level of undissolved solids in bulk fluids. It is also essential this be done in real time, thus, on-line or at-line. Currently, there are many commercial optical devices on the market which can determine particulate concentration in fluids. Measuring instruments used on-line generally use light scattering methods. This technique is very limited as the undissolved solids must be very reflective and of uniform size and shape. It also has a very limited range, usually under 0.1% total undissolved solids.

Ultra sound has also been applied for the measurement of undissolved solids in bulk aqueous solutions, such as water treatment and municipal waste treatment facilities. Limitations of this technique include: 1) the particles must be of uniform size and shape; 2) a maximum temperature of 50 C. for the process solution as temperatures above that change the physical parameters of the focusing lenses and 3) organic solvents can swell or dissolve the polymer focusing lenses required for these systems.

The most commonly applied methods employ off-line gravimetric techniques. A given volume of sample is filtered to remove the liquid. The residue is then weighed. The weight of the residue versus the bulk sample determines the undissolved solids concentration. This technique is time consuming, not usually within the real time of the process and requires expensive manual labor.

SUMMARY OF THE INVENTION

The present invention provides a differential densitometer, for continuously measuring total undissolved solids in a liquid, comprising:
 a) a first densitometer having liquid inflow and outflow means;
 b) a second densitometer having liquid inflow and outflow means; and
 c) filtering means, preferably a cross flow filter, connecting the outflow means of the first densitometer to the inflow means of the second densitometer.

With the above differential densitometer weight percent undissolved solids in a reaction process stream can be measured intermittently or continuously. Such a method comprise the steps of:
 a) providing the above densitometer;
 b) directing at least a portion of the reaction process stream through the first densitometer, the filtering means and then the second densitometer; and
 c) taking the densitometer measurements of both densitometers; and
 d) determining the percent undissolved solids in the reaction process from the difference in the measurements.

A specified weight percent undissolved solids can be maintained in a reaction stream by:
 a) providing the above densitometer;
 b) continuously directing at least a portion of the reaction process stream through the first densitometer, the filtering means and then the second densitometer; and
 c) taking the densitometer measurements of both densitometers; and
 d) determining the percent undissolved solids in the reaction process from the difference in the measurements; and
 e) adjusting the amount of undissolved solids added to the reaction process stream to adjust the determined weight percent undissolved solids to the specified weight percent undissolved solids.

The foregoing methods can be operated continuously as will be shown in the detailed description of the invention.

DETAILS OF THE INVENTION

The apparatus provided by this invention is useful in any chemical process in which it is important to know the concentration of undissolved solids. For purposes of illustration the utility of the invention is demonstrated in the context of a silver nitrate purification process.

Crude silver nitrate solution is formed by mixing nitric acid and crude silver in a vessel in the presence of heat as is done conventionally. Such a process is described for example in U.S. Pat. No. 5,000,928. The silver used as starting material can come from a variety of sources, and any of a very large number of metallic contaminants, as well as non-metallic impurities, may be associated therewith. Silver bars having a purity of 99.0 to 99.99 percent serve as a useful starting material.

Figure 1:
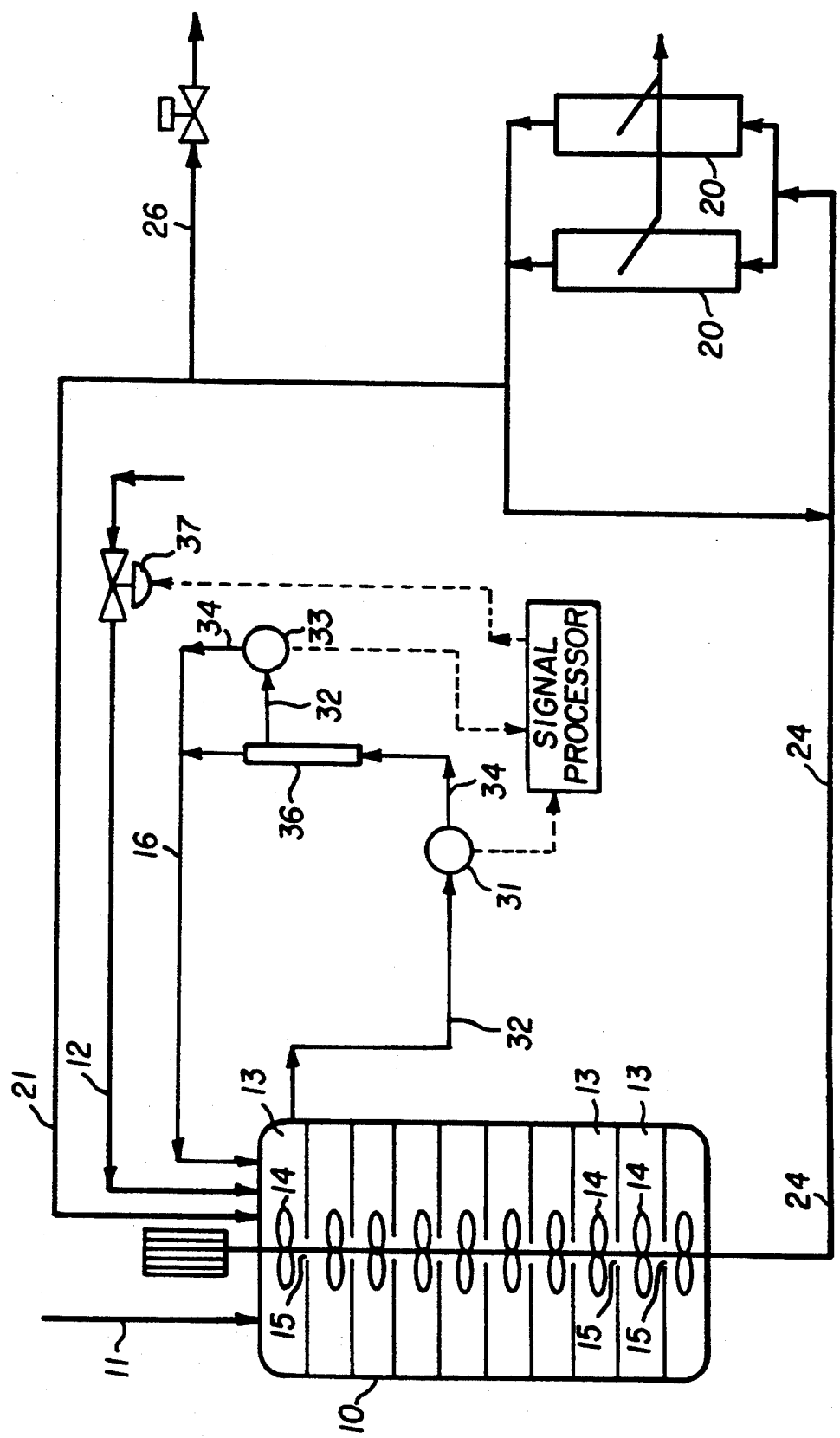
FIG. 1 is a schematic of chemical purification process in which utility of the differential densitometer of the present invention is demonstrate.

FIG. 1 is a schematic diagram of the continuous process of separating impurities from crude silver nitrate solutions that is the subject of this invention. The process is made continuous by the use, in combination, of a continuous multistage agitated reactor column 10, cross flow filtration elements 20, control of weight percent undissolved solids in the column with densitometers 31 and elevated heat in the reactor column. In the separation process crude silver nitrate is delivered continuously to the top of reactor column 10 through line 11. At the same time a slurry comprising an alkalizing agent such as silver oxide is delivered to the top of the reactor through line 12. Other useful alkaline agents include: alkali metal hydroxides such as sodium hydroxide, potassium hydroxide and lithium hydroxide; alkali metal carbonates such as sodium carbonate; alkaline earth metal oxides such as calcium oxide; alkaline earth metal carbonates such as calcium carbonate; alkaline earth metal hydroxides such as calcium hydroxide; and heavy metal hydroxides such as ferric hydroxide. Addition of an alkaline agent, such results in precipitation of metallic contaminants in various forms as is well known in this art.

The continuous multi-staged agitated reactor column replaces the batch reactor tanks used in prior art methods of removing impurities from crude silver nitrate solutions. This kind of reactor is known in the chemical processing industry, but its use in purifying silver nitrate is novel. This type of reactor allows continuous processing to be done without incurring a high inventory cost. Reaction times of 30 minutes to 60 minutes are preferred. Reaction times of 15 minutes to 3 hours can also be used. The reactor column consists of several separate mixing compartments or stages 13. Each stage has its own mixing impeller 14. The stages are connected to each other through opening 15 that traverse the entire reactor. The crude silver nitrate and silver oxide slurry are mixed in the first stage and mixed and continuously in each stage in the reactor column as the mixture passes down the column through opening 15. Total residence time of the mixture of crude silver nitrate and silver oxide slurry is from 15 minutes to 3 hours and usually 30 to 60 minutes. Total residence time will depend upon the level of impurities in the crude silver nitrate, reaction rates in the column and the temperature at which the reactions are conducted. During the residence time the reactor column is maintained at temperatures up to the boiling point of the mixture. Generally temperatures in the range of 40° to 80° C. will be useful. The elevated temperatures greatly enhances the rate of precipitation of impurities. Elevated temperatures forces reactions to proceed at maximum rates. This helps to minimize the working inventory of crude silver required in prior art processes. Increase reaction rates This also contributes to making the process of the invention continuous.

The mixture in the reactors comprises crude silver nitrate solution, solid silver oxide and other solids that are fed into the top of reactor column 10 through slurry return line 21 from the filtration process discussed in detail below. We have found that maximum reaction rates and precipitation of impurities are enhanced by maintaining 0.5 to 8 weight percent undissolved solids, preferably 2 weight percent, throughout the entire reactor column during the process. This range of weight percent undissolved solids are designed to maintain 0.2 to 1.6 weight percent silver oxide in the reaction column. This means that silver oxide is maintained at a level of 10 to 80 weight percent of the total undissolved solids, as determined from time to time, by off line analysis of the slurry.

This targeted weight percent undissolved solids is maintained continuously using a differential density instrument programmed in combination with a computerized signal processor conventionally used to control chemical processes. The instrument, in conjunction with the signal processor, uses commercially available separators and densitometers to separate a clarified solution from the process stream, and to calculate the difference in density between the whole and the clarified slurries. The signal processor is programmed to adjust the amount of silver oxide fed to the reactor column through line.

The differential density instrument uses commercially available separators and densitometers to separate a clarified solution from the process stream, and to calculate the difference in density between the whole and the clarified slurries. The difference in density is then proportional to the concentration of solid reagents in the reactor. Two density measurements are required because a single measurement cannot distinguish between dissolved and undissolved solids. This type of analyzer gives a real-time analysis of the reaction mixture to allow close control of the process.

In FIG. 1 a schematic drawing is presented of an on-line arrangement of a differential, densitometer, according to the invention, for maintaining a targeted weight percent undissolved solids in chemical processes. In the method on-line determination of weight percent undissolved solids is accomplished by measuring the weight percent undissolved solids in the mixture in the first stage of the reactor column. This is done by first measuring the density of the mixture, filtering the mixture and then measuring the density of the resulting filtrate. The difference in density is proportional to the undissolved solids present in the mixture.

Figure 2:
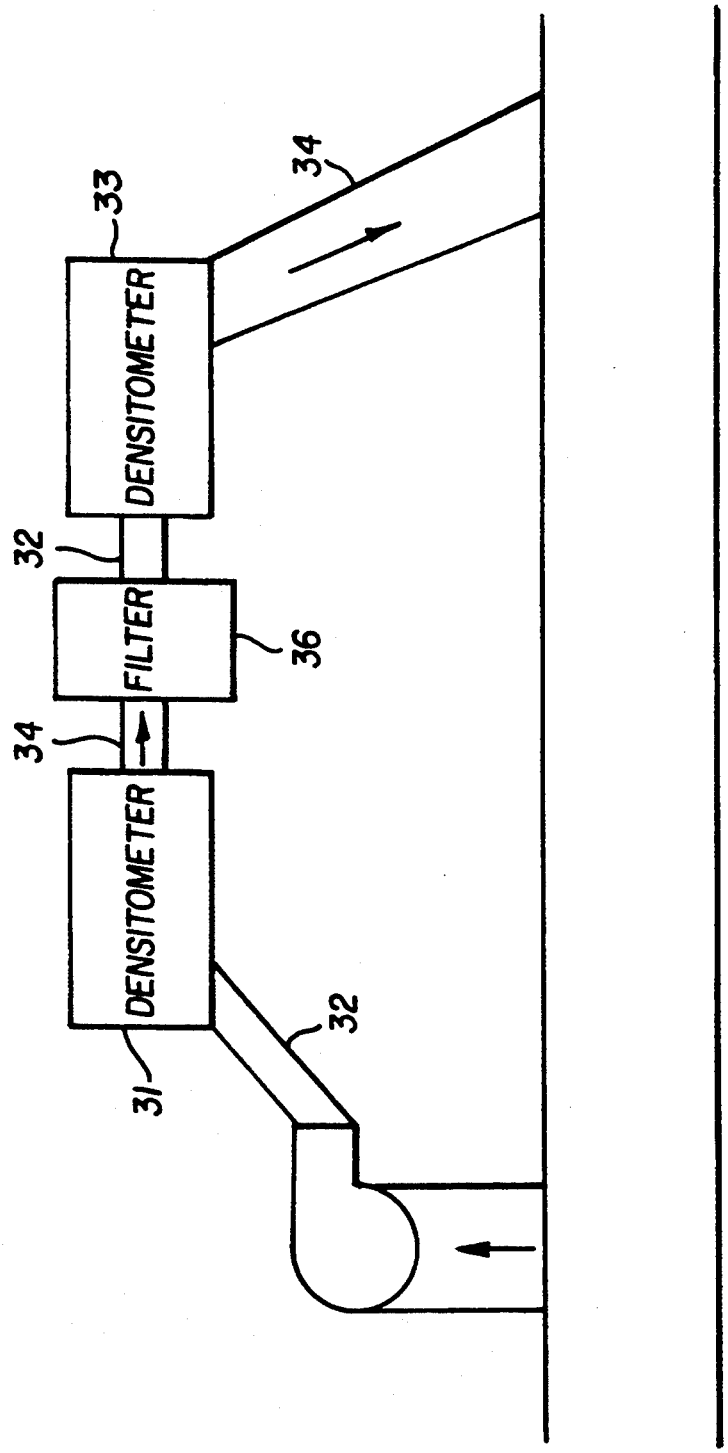
FIG 2 is a schematic of a differential density densitometer used in a process.

In FIG. 2 a schematic of the differential densitometer of FIG. 1 is shown for obtaining the differential density measurement. The apparatus consists of a first densitometer 31 having inflow and outflow means 32 and 34, and a second densitometer 33, having similar inflow means 32 and outflow means 34. Outflow means 34 of the first densitometer 31 is fluidly connected to a filter 36, preferably a crossflow filter. The filter is fluidly connected to outflow means 34 of the first densitometer. The filter 36 and the outflow means 34 of the second densitometer are connected to a return line 21 (not shown) that returns the sample to the reactor column. This arrangement provides for real time on-line measurement of density continuously as the reaction mixture moves through the reactor column.

Referring again to FIG. 1, a sample of the mixture from the first stage of the reactor column is pumped via inflow means 32 through the first densitometer 31 where a first density reading is taken and fed electronically to the signal processor. The sample is then pumped via out flow means 34 though filter 36 to remove undissolved solids. The removed undissolved solids are pumped to line 16. The filtrate is pumped into the second densitometer 31 where a second density reading is taken and fed electronically to the signal processor. The filtrate is then pumped back to return line 16. Many densitometers are available commercially which can be used in this process. This density gauge measures density of a solution flowing through it, and a 4–20 amps signal which is proportional to the density is sent to the signal processor. The signal processor computes the difference in densitometer readings and compares that difference to a look up table or digitally compares the values to a pre-established calibration and then adjusts the input of the silver oxide slurry into the reactor column according to a pre-established target value that adjusts weight percent undissolved solids to the concentration targeted for the process of this invention.

The reaction mixture emerges from the bottom of reactor column 10 through line 24 and is pumped continuously through line 24 to a pair cross flow filters. The settling and cartridge filtration separation step of batch processes of the prior art is replaced by continuous cross flow filtration. Any cross flow filter arrangement will be useful. The filtering process produces a first silver nitrate solution. Cross flow filters are known in the art and are available commercially from a variety of sources. Continuous filtration significantly reduces the in process silver inventory required in prior art batch methods. Cross flow filtration is superior to the settling and filtering arrangement used in the prior art batch methods. It produces more particulate free silver nitrate solution and therefore fewer impurities in the filtered silver nitrate solution. Moreover, cross flow filtration promotes good filtrate flow flux rate. This is surprising due to the fast fouling rates observed with cake filtration equipment. The preferred filter is a crossflow ceramic membrane filter. This type of filter has the advantage of being highly corrosion resistant at the temperature required to operate the reactions at good reaction rates.

Continuous filtration produces a slurry mixture of silver nitrate solution, silver oxide solids and impurity solids. This mixture contains a higher weight percent undissolved solids than that fed to multi-stage reactor column. The concentration of undissolved solids in the filter is controlled by returning slurry to the top of the multi-stage reactor via line 21. This allows for reuse of silver oxide that has not been reacted. A portion of the slurry is also purged from the process through line 26 such that silver oxide is maintained in the slurry between 10 to 80 weight percent. This purge is critical for controlling the amount of silver oxide undissolved solids in the system and the most consistent operation is obtained when the rate of impurity undissolved solids accumulated equals the rate of which the rate of impurity undissolved solids are purged.

The silver nitrate filtrate resulting from the foregoing process may be subjected to a second continuous purification treatment that is identical to the process described above. This includes subjection to a second multi-staged reactor column, control of weight percent undissolved solids and filtration. In this second purification a slurry containing both silver oxide and a flocculant, such as iron nitrate, iron oxide, iron powder and other such flocculants known in the art, is fed to the reactor column with the first silver nitrate filtrate. The result is an ultra pure silver nitrate solution.

The invention has been described in detail with particular reference to preferred embodiments thereof, but it will be understood that variations and modifications can be effected within the spirit and scope of the invention.

We claim:

1. A differential densitometer for continuously measuring total undissolved solids in a liquid comprising:
   a) a first densitometer having liquid inflow and outflow means;
   b) a second densitometer having liquid inflow and outflow means; and
   c) filtering means connecting the outflow means of the first densitometer to the inflow means of the second densitometer.

2. The densitometer of claim 1 wherein the filter is a cross flow filter.

3. The densitometer of claim 2 wherein the filter is ceramic.

4. A method of maintaining a specified weight percent undissolved solids in a reaction process stream to which undissolved solids may be added, comprising the steps of;
   a) providing a differential densitometer comprising:
      i) a first densitometer having liquid inflow and outflow means;
      ii) a second densitometer having liquid inflow and outflow means; and
      iii) filtering means connecting the outflow means of the first densitometer to the inflow means of the second densitometer;
   b) continuously directing at least a portion of the reaction process stream through the first densitometer, the filtering means and then the second densitometer; and
   c) taking the densitometer measurements of both densitometers;
   d) determining the percent undissolved solids in the reaction process from the difference in the measurements; and
   e) adjusting the amount of undissolved solids added to the reaction process stream to adjust the determined weight percent undissolved solids to the specified weight percent undissolved solids.

5. A method of measuring weight percent undissolved solids in a reaction process stream, comprising the steps of:
   a) providing a differential densitometer comprising:
      i) a first densitometer having liquid inflow and outflow means;
      ii) a second densitometer having liquid inflow and outflow means; and
      iii) filtering means connecting the outflow means of the first densitometer to the inflow means of the second densitometer;
   b) directing at least a portion of the reaction process stream through the first densitometer, the filtering means and then the second densitometer; and
   c) taking the densitometer measurements of both densitometers; and
   d) determining the percent undissolved solids in the reaction process from the difference in the measurements.

6. A method of continuously maintaining a specified weight percent undissolved solids in a reaction process stream to which undissolved solids are continuously added, comprising the steps of;
   a) providing a providing a differential densitometer comprising:
      i) a first densitometer having liquid inflow and outflow means;
      ii) a second densitometer having liquid inflow and outflow means; and
      iii) filtering means connecting the outflow means of the first densitometer to the inflow means of the second densitometer;
   b) continuously directing at least a portion of the reaction process stream through the first densitometer, the filtering means and then the second densitometer; and
   c) continuously taking the densitometer measurements of both densitometers;
   d) continuously determining the percent undissolved solids in the reaction process from the difference in the measurements: and
   e) continuously adjusting the amount of undissolved solids added to the reaction process stream to adjust the determined weight percent undissolved solids to the specified weight percent undissolved solids.

7. The method of claim 4 and 6 wherein the measurements, measurement differences and adjustments to the undissolved solids flowing into the reaction process are carried out continuously through a signal processor capable of receiving two analog signals, ratio the two signal, and compare the difference to a lookup table or digitally compare the signals to a pre established calibration curve.

* * * * *